United States Patent
He et al.

(10) Patent No.: US 10,380,792 B2
(45) Date of Patent: Aug. 13, 2019

(54) THREE-DIMENSIONAL MODEL GENERATION

(71) Applicant: HEWLETT-PACKARD DEVELOPMENT COMPANY, L.P., Houston, TX (US)

(72) Inventors: Jack Hui He, Fort Collins, CO (US); Paul Howard Mazurkiewicz, Fort Collins, CO (US); Hang-Yan Yuen, Fort Collins, CO (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/567,314

(22) PCT Filed: Sep. 30, 2015

(86) PCT No.: PCT/US2015/053094
§ 371 (c)(1),
(2) Date: Oct. 17, 2017

(87) PCT Pub. No.: WO2017/058187
PCT Pub. Date: Apr. 6, 2017

(65) Prior Publication Data
US 2018/0197328 A1 Jul. 12, 2018

(51) Int. Cl.
*G06T 17/00* (2006.01)
*G01J 3/44* (2006.01)
*G01N 21/31* (2006.01)
*G06F 17/50* (2006.01)
*G06T 19/20* (2011.01)

(52) U.S. Cl.
CPC ............ *G06T 17/00* (2013.01); *G01J 3/44* (2013.01); *G01N 21/31* (2013.01); *G06F 17/50* (2013.01); *G06T 19/20* (2013.01)

(58) Field of Classification Search
None
See application file for complete search history.

(56) References Cited

U.S. PATENT DOCUMENTS

| 5,127,037 A | 6/1992 | Bynum |
| 5,301,117 A * | 4/1994 | Riga ............... G05B 19/4207 623/901 |

(Continued)

FOREIGN PATENT DOCUMENTS

WO WO2015077077 5/2015

OTHER PUBLICATIONS

Shackley, M. Steven. "X-Ray Fluorescence Spectrometry (XRF)." the Encyclopedia of Archaeological Sciences (2011): 1-5.*

(Continued)

*Primary Examiner* — Ryan M Gray
(74) *Attorney, Agent, or Firm* — HP Inc. Patent Department (57) ABSTRACT

Examples associated with three-dimensional model generation are disclosed. One example includes analyzing a structure of a first component of an object. The composition of the first component of the object is also analyzed. A three-dimensional model of the object is then generated. The three-dimensional model includes data based on the structure of the first component of the object and data based on the composition of the first component of the object.

18 Claims, 7 Drawing Sheets

(56) References Cited

U.S. PATENT DOCUMENTS

| | | | |
|---|---|---|---|
| 7,373,286 B2* | 5/2008 | Nikolskiy | G06F 19/321 703/7 |
| 9,767,226 B2* | 9/2017 | Chen | G06F 17/5009 |
| 2008/0225044 A1* | 9/2008 | Huang | G06T 17/00 345/420 |
| 2010/0098328 A1* | 4/2010 | Se | G01C 11/06 382/154 |
| 2010/0203478 A1 | 8/2010 | Rubbert | |
| 2011/0087350 A1 | 4/2011 | Fogel | |
| 2012/0277899 A1 | 11/2012 | Chun et al. | |
| 2013/0066812 A1 | 3/2013 | Nehme | |
| 2014/0046469 A1 | 2/2014 | Bickel et al. | |
| 2014/0052285 A1 | 2/2014 | Butcher et al. | |
| 2014/0324204 A1* | 10/2014 | Vidimce | B29C 67/0088 700/98 |
| 2015/0045928 A1 | 2/2015 | Perez et al. | |
| 2015/0096266 A1 | 4/2015 | Divine et al. | |
| 2016/0025657 A1* | 1/2016 | Shahbazmohamadi | G10D 9/02 378/20 |
| 2016/0301910 A1* | 10/2016 | Lucas | G06T 17/00 |
| 2017/0008085 A1* | 1/2017 | Nguyen | B28B 1/001 |
| 2017/0085733 A1* | 3/2017 | Ilic | G06T 19/20 |

OTHER PUBLICATIONS

Ottena, et al; "Combining X-Ray CT and 3D Printing Technology to Produce Microcosms with Replicable, Complex Pore Geometries"; Aug. 2012; http://www.sciencedirect.com/science/article/pii/S0038071712001472.

* cited by examiner

THREE-DIMENSIONAL MODEL GENERATION

BACKGROUND 3D printers are used to generate three dimensional objects. One of many techniques used for 3D printing, sometimes referred to as additive manufacturing, involves successively layering material based on control from a computer relying on a 3D model. 3D printers are used across a wide variety of industries (e.g., automobiles, construction, research, medicine) and may be used, for example, for prototyping, making emergency replacement parts, recreation, and so forth. A wide variety of materials may be used for 3D printing, each having different attributes when formed into a completed object.

BRIEF DESCRIPTION OF THE DRAWINGS

The present application may be more fully appreciated in connection with the following detailed description taken in conjunction with the accompanying drawings, in which like reference characters refer to like parts throughout, and in which.

DETAILED DESCRIPTION

Systems, methods, and equivalents associated with three-dimensional model generation are described. As discussed above, 3D printers may be used to create reproductions of objects from 3D models. Sometimes these models are generated using specialized computer aided design applications. Other times, these models are generated directly by scanning or imaging physical objects. Consequently, a 3D printer may be able to create reproductions of other physical objects. However, in some instances, it may be desirable to not only recreate the physical shape of the object in the reproduction, but also recreate certain physical properties of the original object. These physical properties may range from color, to structural, physical, and mechanical attributes, to how the reproduction will interact with other items or chemicals with which the reproduction will come into contact depending how the reproduction will be used, and so forth.

One way to recreate physical properties of an original object in a reproduction is to determine the composition of the original object (e.g., elements or molecules making up the object), or information related to the composition of the object (e.g., properties of a composition if a specific chemical makeup of the object cannot be specifically identified). This may be achieved by various techniques, including various X-ray spectroscopic techniques. By way of illustration, in X-ray fluorescence spectroscopy, a beam bombards atoms of an object with energy to cause those atoms to emit photons that can be measured to identify what type of elements are in an object. By learning the composition of the original object, a 3D model of that object may be generated so that when a reproduction of the object is made, composition information for the object may be determined directly from the 3D model, and used in the reproduction.

Consequently, it may be desirable to be able to generate 3D models of objects that includes compositions of the objects by directly scanning compositions of objects. Being able to identify compositions of objects may also be desirable when creating reproductions of objects made of multiple materials. For example, a 3D printer capable of printing with multiple materials may be able to make an entire reproduction of an object with multiple materials at once, without them later having to be separately assembled. For example, some fused deposition modeling 3D printing systems may be able to generate 3D objects from multiple materials.

Figure 1:
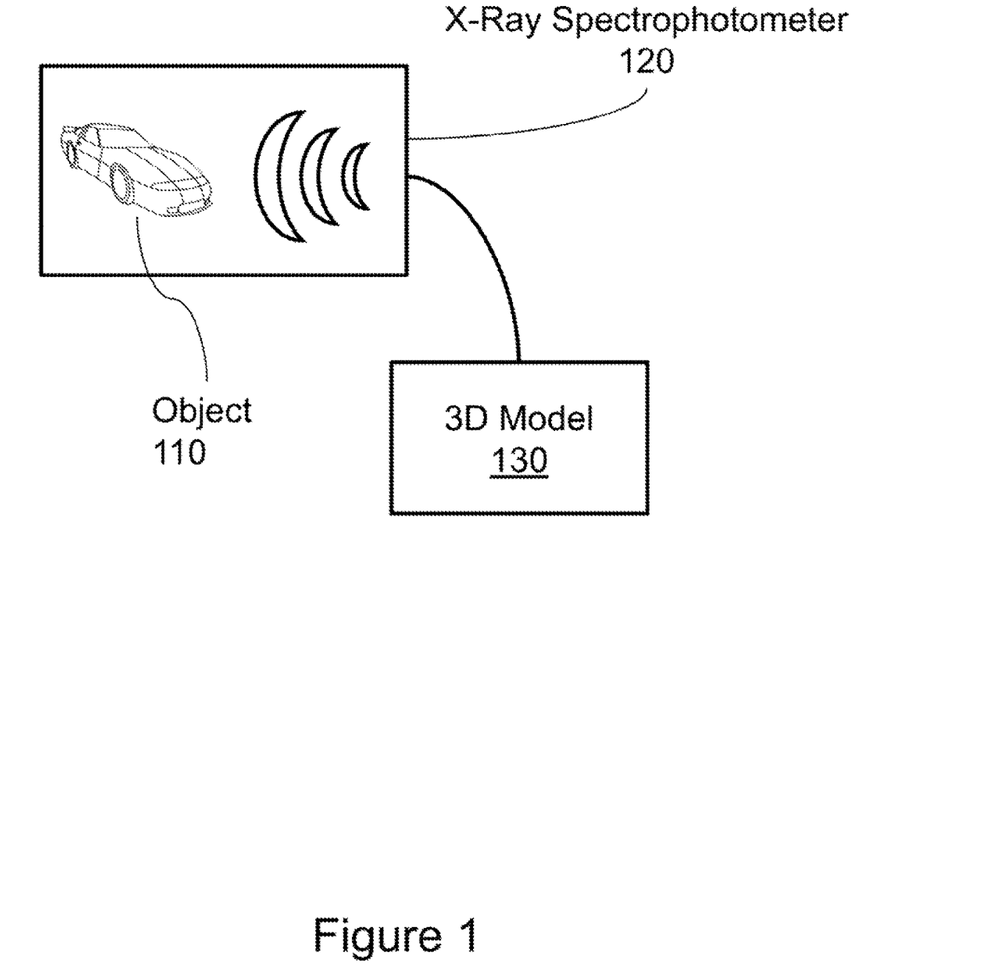
FIG. 1 illustrates an example X-Ray Spectrophotometer associated with three-dimensional model generation.

FIG. 1 illustrates an example X-Ray Spectrophotometer associated with three-dimensional model generation. It should be appreciated that the items depicted in FIG. 1 are illustrative examples and many different devices, and so forth may operate in accordance with various examples.

FIG. 1 illustrates an example X-Ray Spectrophotometer 120 associated with 3-dimensional model generation (henceforth referred to as X-Ray 120). In this example, X-ray 120 is in the process of scanning an object 110, and generating a 3D model 130 of object 110. In this example, a toy car is used to represent object 110 although numerous other objects may be used.

As used herein a reproduction is used to refer generally to an object generated by a 3D printer. In the context of this application a reproduction will often be produced as a near approximate copy of a specific physical object that is being copied. However, in some examples, a differences between the reproduction and the original object may be introduced between scanning the object and producing the reproduction. These differences may be the result of, for example, unavailability of a material that exactly matches a composition of a component of the object, physical limitations of a 3D printer that result in imperfections to the reproduction, and even redesign of the object (e.g., by a user via a computer interface) before producing the reproduction. This redesign may include modifying sizes, shapes, and other attributes of the original object prior to producing the reproduction.

Consequently, a reproduction made (e.g., via a 3D printing process) may be a copy of object 110. To create the reproduction, a 3D printer may rely on three-dimensional model 130 of object 110. In various examples, 3D model 130 may control a 3D printer to construct a reproduction of object 110 according to the data within 3D model 130. Though 3D model 130 could be obtained from a variety of sources, in this example, the 3D model is generated based on data received from an X-Ray 120. Though examples involving 3D printing are described herein, it is possible that 3D model 130 could be used for other purposes, such as in manufacturing process that do not involve a 3D printer. Further, other uses of 3D model 130 outside of manufacturing may also exist, such as in simulating certain attributes of object 110 in a virtual reality environment (e.g., light effects, physics, interactions with users or other virtual objects).

Here, X-Ray 120 is used to identify both structural features of object 110, as well as the composition of components of object 110. These structural features and compositions may include and/or be based on surface attributes of object 110, internal attributes of object 110, a combination of the two, and so forth. By way of illustration, in some examples, where object 110 is a solid object, physical attributes such as the shape of object 110 may be identified using techniques that scan the surface of object 110. In these examples, the composition of object 110 may be obtained by scanning a small portion at the surface of object 110. In more sophisticated examples, where object 110 is more complex (e.g., including internal sub-structures), the physical attributes of various sub-structures may be obtained using a first set of techniques, and the compositions of the sub-structures may be obtained using a second set of techniques. The toy car (object 110) illustrated in FIG. 1 may be an example of a more complex example as the toy car may be made of several components (e.g., wheels, axels, and body that are independent of one another and made of different materials).

As used herein, physical attributes of an object generally refer to, for example, sizes and shapes of the object, sizes and shapes of components of the object, interfaces between components of the object, surface textures of object the, and so forth. Physical attributes in some cases may also include other attributes of an object that are otherwise identifiable without knowing, for example, what ratios of molecules and/or atoms makeup components of the object. For example, a surface color of the object that is detectable via, for example, an optical sensor may be considered a physical attribute of the object. As used herein, the composition of an object may refer to materials from which the object is made. Depending on which technique is used to identify the composition of the object, the composition may be described in terms of elemental composition (e.g., ratios of different periodic elements), molecular composition (e.g., ratios of different molecules), and so forth. Certain techniques may also identify densities of materials at various points of an object, and therefor other attributes of objects that can be identified by scanning types, quantities, distributions, and so forth of elements and/or molecules of an object are considered a part of the composition of an object. Distinctly, when the term chemical composition is used, this is intended to refer generally to which specific materials, molecules, and/or elements an object is made up of. Generating 3D models 130 having both physical attributes and compositions may facilitate creating a more accurate reproductions of objects 110 because the reproductions may share not only shapes of objects 110, but also other physical properties of the objects 110.

Though in this example an X-Ray 120 is shown, there are many other ways by which compositions of components of object 110 may be identified. A non-exhaustive list includes, for example, optical imaging and scanning, microscopy, x-ray fluorescence (XRF), infrared spectroscopy, Raman spectroscopy, ultra-violet spectroscopy, ultraviolet-visible spectroscopy, laser induced breakdown spectroscopy, and so forth. Depending on the technique used, compositions may be identified at the elemental level, the molecular level, or other levels.

It is appreciated that, in the following description, numerous specific details are set forth to provide a thorough understanding of the examples. However, it is appreciated that the examples may be practiced without limitation to these specific details. In other instances, methods and structures may not be described in detail to avoid unnecessarily obscuring the description of the examples. Also, the examples may be used in combination with each other.

"Module", as used herein, includes but is not limited to hardware, firmware, software stored on a computer-readable medium or in execution on a machine, and/or combinations of each to perform a function(s) or an action(s), and/or to cause a function or action from another module, method, and/or system. A module may include a software controlled microprocessor, a discrete module, an analog circuit, a digital circuit, a programmed module device, a memory device containing instructions, and so on. Modules may include gates, combinations of gates, or other circuit components. Where multiple logical modules are described, it may be possible to incorporate the multiple logical modules into one physical module. Similarly, where a single logical module is described, it may be possible to distribute that single logical module between multiple physical modules.

Figure 2:
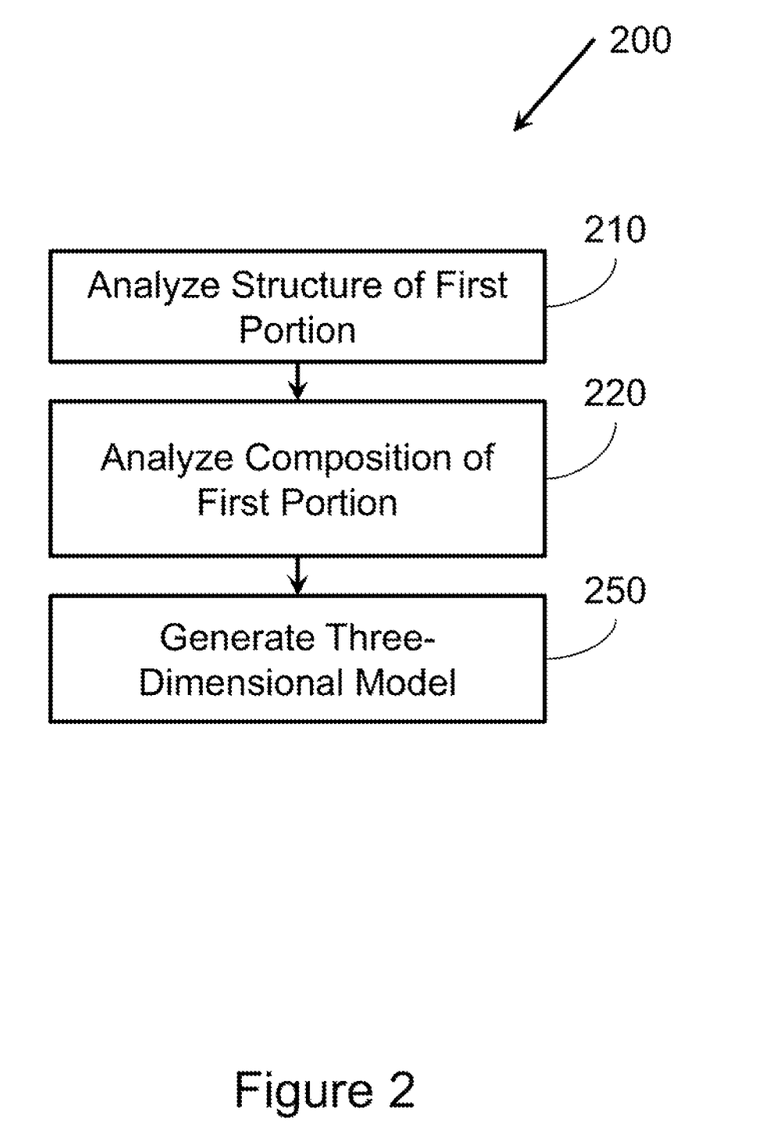
FIG. 2 illustrates a flowchart of example operations associated with three-dimensional model generation.

FIG. 2 illustrates an example method 200 associated with three-dimensional model generation. Method 200 may be embodied on a non-transitory computer-readable medium storing computer-executable instructions. The instructions, when executed by a computer, may cause the computer to perform method 200. In other examples, method 200 may exist within logic gates and/or RAM of an application specific integrated circuit.

Method 200 includes analyzing a structure of a first portion of an object at 210. A portion of the object may include, for example, the entirety of the object, a specific substructure of the object, a region of the object, and so forth. In some examples, an X-Ray may be used to analyze the structure of the first portion. In other examples, other technologies may be used for analyzing the physical structure of the first portion. As used herein, the structure of the first portion refers generally to shapes, sizes, physical relationships, and so forth that are related to the actual form of the physical object. Properties of the object related to, for example, hardness of the portion, may not be identifiable by a scan of the structure of the first portion, but may be determined based on a composition of the first portion.

Method 200 also includes analyzing a composition of the first portion of the object at 220. In various examples, the composition of the first portion may be analyzed using, for example, optical imaging and scanning, microscopy, x-ray fluorescence (XRF), infrared spectroscopy. Raman spectroscopy, ultra-violet spectroscopy, ultraviolet-visible spectroscopy, laser induced breakdown spectroscopy, and so forth. Depending on the techniques used, the composition may refer to ratios of elements found in the first portion, ratios of molecules found in the first portion, densities of molecules found in the first portion, arrangement of molecules found in the first portion, and so forth. In some examples, depending on the analysis technique used at action 220, the composition obtained may be a chemical composition of the first portion of the object.

Method 200 also includes generating a three-dimensional model of the object at 250. The three-dimensional model may include data based on the structure of the first portion of the object based on analysis performed at action 210. In some examples, the data based on the structure of the first portion of the object may describe both internal and surface structure of the first portion of the object. On the other hand, more complex analysis may be desirable to identify an internal structure of more complex objects (e.g., a chest of drawers, a soda can due to the hollow cavity, a toy car). The three-dimensional model may also include data based on the composition of the first portion of the object based on analysis performed at action 220. As with the physical structure of the first portion of the object, the data based on the composition of the first portion of the object may describe both internal and surface composition of the object.

Depending on how detailed the three-dimensional model is generated, different techniques for describing both the physical structure and composition of portions of the object may be used. By way of illustration, for simple solid objects (e.g., a cube, a cylinder, objects that can be described by a set of mathematical equations), dimensions of these objects may be sufficient for describing the physical structure of the object in the three-dimensional model. For more complex objects, physical structure of the object may be represented by voxels, which represent points in a three-dimensional space. Each voxel may represent a small portion of the object much in the same way that a pixel represents a small portion of a two-dimensional picture. In the context of the three-dimensional model representing the first portion of the object voxels may include, for example, location information, whether the three-dimensional space taken up by the voxel takes up the entire space associated with the voxel (e.g., to deal with a bevel or curve of the object), and so forth. Additionally, to preserve composition information, each voxel in the three-dimensional space may also include information describing composition of materials from the object at that location.

Figure 3:
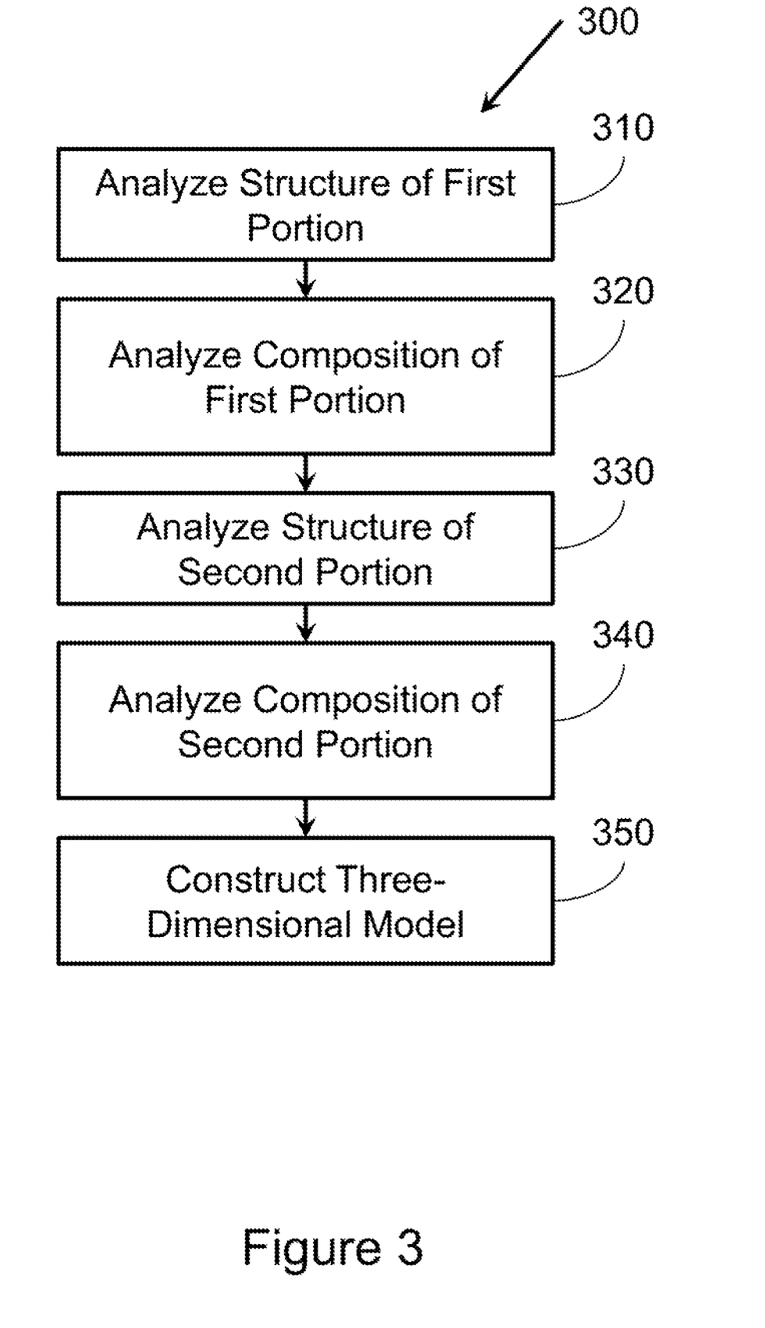
FIG. 3 illustrates another flowchart of example operations associated with three-dimensional model generation

FIG. 3 illustrates another example method 300 associated with three-dimensional model generation. Method 300 includes several actions similar to those described above with reference to method 200 (FIG. 2). For example, method 300 includes analyzing a structure of a first portion of an object at 310, analyzing a composition of the first portion at 320, and generating a three-dimensional model of the object at 250.

Method 300 also includes analyzing a structure of a second portion of the object at 330. Method 300 also includes analyzing the composition of the second portion of the object. In this example, the three-dimensional model of the object also includes data based on the structure of the second portion of the object, as well as data based on the composition of the second portion of the object.

In various examples, the of the first and second portion's physical structures and/or the first and second portion's compositions may be combined in various combinations and performed in fewer than the number of actions distinctly illustrated in method 300. Whether this is possible, or desirable may depend on the techniques used for analyzing physical structures and/or compositions of the object and its portions. As an example, analyzing the physical structure of the first portion and analyzing physical structure of the second portion may be performed by one technique for analyzing physical structures of objects. Similarly, compositions of the first and second actions may be analyzed in a single discrete action. However, if a composition analysis technique aggregates data for simultaneously analyzed portions, it may be desirable to perform this technique separately on the first portion and the second portion to determine if these portions have the same or different compositions.

Figure 4:
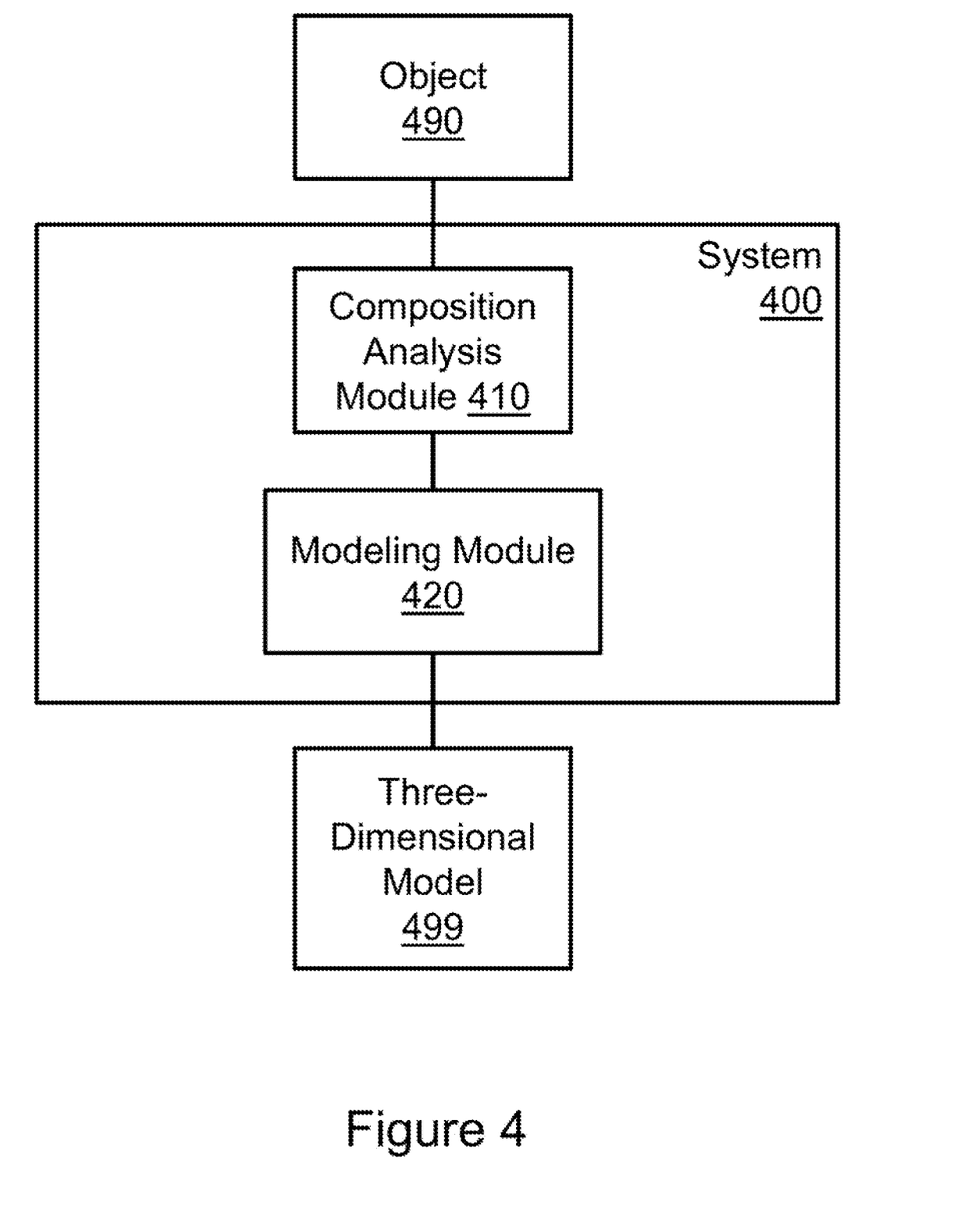
FIG. 4 illustrates an example system associated with three-dimensional model generation.

FIG. 4 illustrates an example system 400 associated with three-dimensional model generation. System 400 includes a composition analysis module 410. Composition analysis module 410 may analyze a structure of an object 490. Composition analysis module 410 may also analyze compositions of components of object 490. Composition analysis 410 module may analyze compositions of components of object 490 using, for example, optical imaging and scanning, microscopy, x-ray fluorescence (XRF), infrared spectroscopy, Raman spectroscopy, ultra-violet spectroscopy, ultraviolet-visible spectroscopy, and laser induced breakdown spectroscopy on the components of the object.

System 400 also includes a modeling module 420. Modeling module 420 may generate a three-dimensional model 499. Three-dimensional model 499 may be generated based on the structure of object 490 and on compositions of components of object 490.

Figure 5:
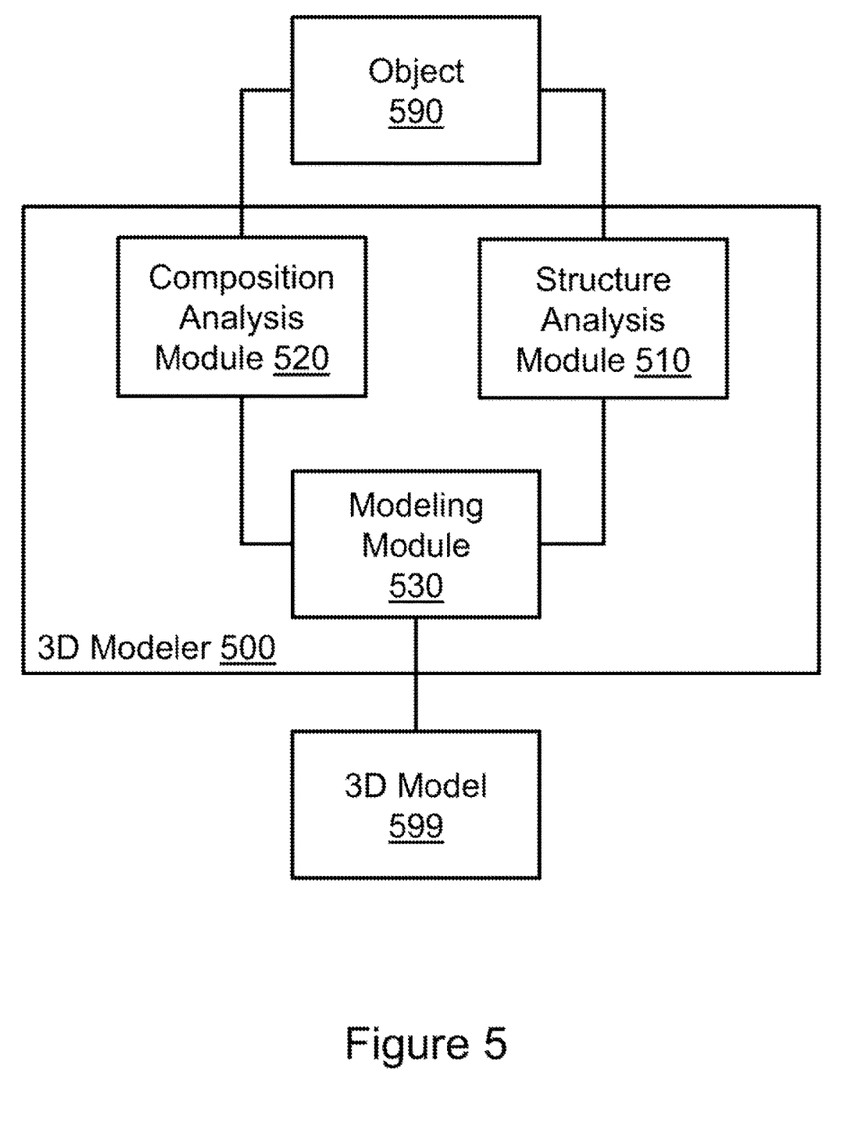
FIG. 5 illustrates an example 3D modeler associated with three-dimensional model generation.

FIG. 5 illustrates a 3D modeler 500. 3D modeler 500 includes a structure analysis module 510. Structure analysis module 510 may analyze a physical structure of an object 590. 3D modeler 500 also includes a composition analysis module 520. Composition analysis module 520 may analyze a composition of object 590.

3D modeler 500 also includes a modeling module 530. Modeling module 530 may generate a three-dimensional model 599 of object 590. Three-dimensional model 599 may include data describing physical attributes of object 590.

The physical attributes may be generated based on the physical structure of object 590 as analyzed by structure analysis module 510. Three dimensional model 599 may also include data describing the composition of object 590. In some examples, three-dimensional model 599 may be characterized by a set of voxels. In these examples, each voxel may have physical attributes and chemical attributes. The physical attributes may be determined based on the physical structure of object 590. The physical attributes may include location attributes, size attributes, and so forth. The chemical attributes may be determined based on the composition of object 590. The chemical attributes may describe materials associated with respective voxels.

Figure 6:
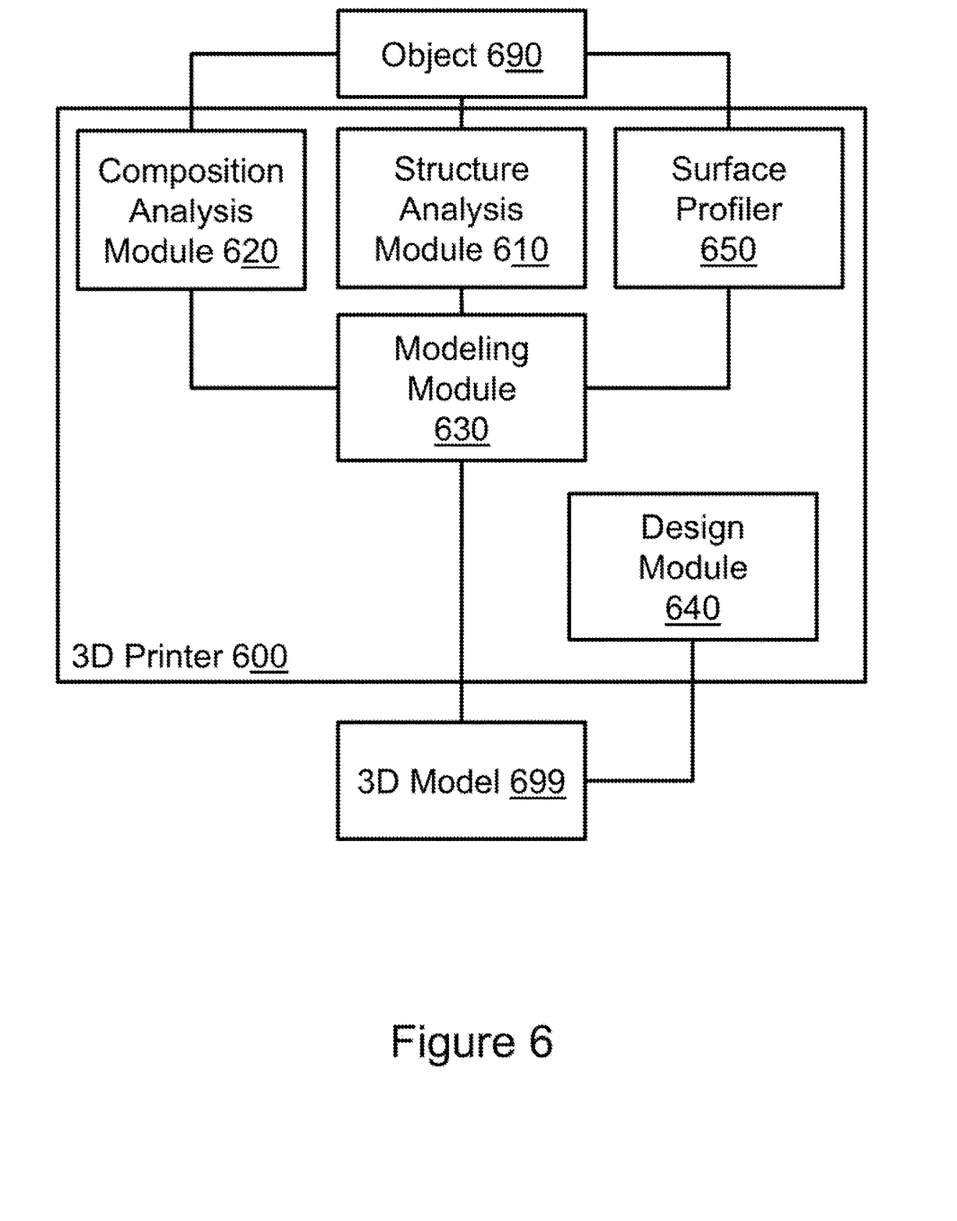
FIG. 6 illustrates another example 3D modeler associated with three-dimensional model generation.

FIG. 6 illustrates a 3D modeler 600. 3D modeler 600 includes several items similar to those described above with reference to 3D modeler 500 (FIG. 5). For example, 3D modeler 600 includes a structure analysis module 610, a composition analysis module 620, and a modeling module 630 to produce a three-dimensional model 699 of an object 690.

3D printer 600 also includes a design module 650. Design module may facilitate modifying three-dimensional model 699. Three-dimensional model 699 may be modified by, for example, a physical structure of a component of three-dimensional model 699. In another example, a composition of a component of three-dimensional model 699 may be changed. Consequently, design module 640 may facilitate adjusting three-dimensional model 699 prior to the use of three-dimensional model 699 in creating a reproduction of object 690. In various examples, design module 640 may be a logic designed to fix or adjust model 699 under certain known circumstances, or a user driven logic to allow adjustments or even complete redesign of three-dimensional model 699 or a portion thereof.

3D printer 600 also includes a surface profiler 650. Surface profiler 650 may analyze surface characteristics, such as surface roughness, of object 690. Consequently, modeling module 630 may generate three-dimensional model 699 of object 690 so that surface components of three-dimensional model 699 have surface roughness that corresponds to the surface roughness of object 690.

Figure 7:
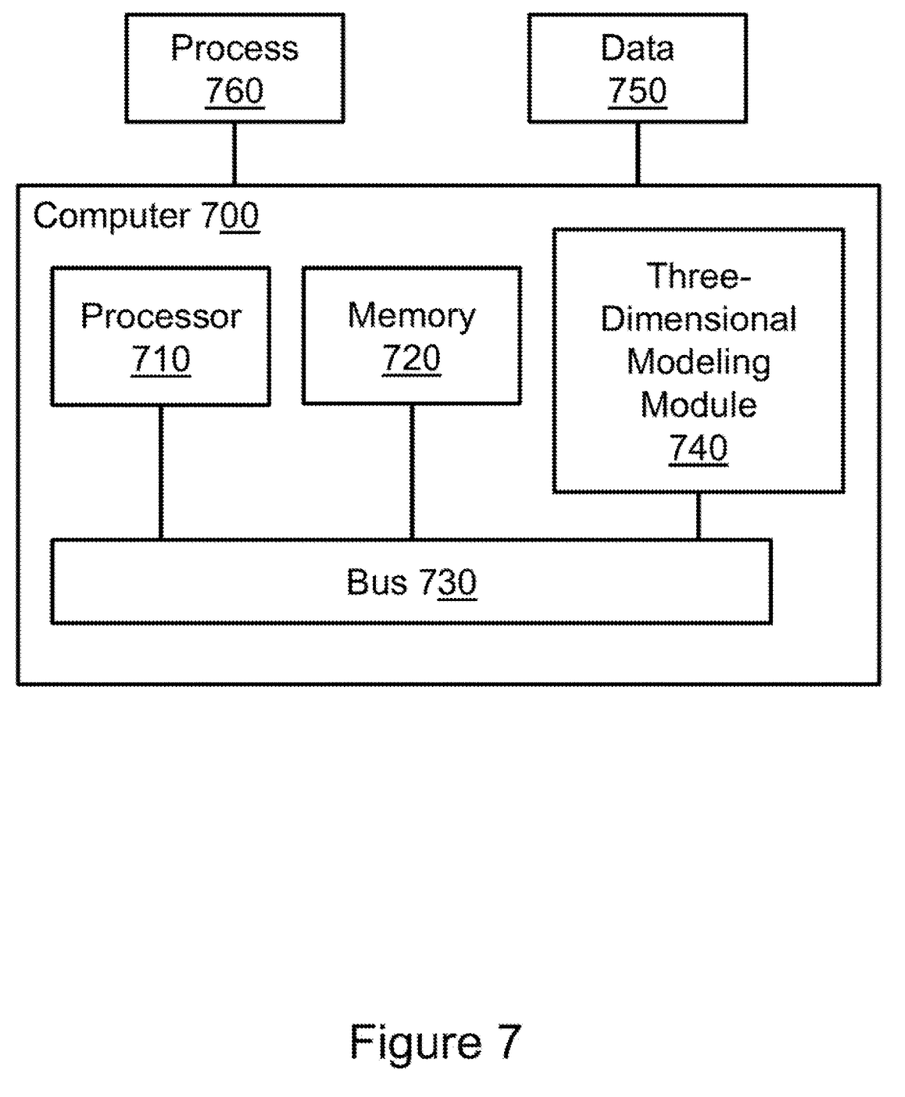
FIG. 7 illustrates an example 3D printer in which example systems, and methods, and equivalents, may operate.

FIG. 7 illustrates an example computer in which example systems and methods, and equivalents, may operate. The example computer may include components such as a processor 710 and a memory 720 connected by a bus 730. Computer 700 also includes a three-dimensional modeling module 740. Three-dimensional modeling module 740 may perform, alone or in combination, various functions described above with reference to the example systems, methods, apparatuses, and so forth. In different examples, three-dimensional modeling module 740 may be implemented as a non-transitory computer-readable medium storing processor-executable instructions, in hardware, software, firmware, an application specific integrated circuit, and/or combinations thereof.

The instructions may also be presented to computer 700 as data 750 and/or process 760 that are temporarily stored in memory 720 and then executed by processor 710. The processor 710 may be a variety of processors including dual microprocessor and other multi-processor architectures. Memory 720 may include non-volatile memory (e.g., read only memory) and/or volatile memory (e.g., random access memory). Memory 720 may also be, for example, a magnetic disk drive, a solid state disk drive, a floppy disk drive, a tape drive, a flash memory card, an optical disk, and so on. Thus, memory 720 may store process 760 and/or data 750. Computer 700 may also be associated with other devices including computers, computers, peripherals, and so forth in numerous configurations (not shown).

It is appreciated that the previous description of the disclosed examples is provided to enable any person skilled in the art to make or use the present disclosure. Various modifications to these examples will be readily apparent to those skilled in the art, and the generic principles defined herein may be applied to other examples without departing from the spirit or scope of the disclosure. Thus, the present disclosure is not intended to be limited to the examples shown herein but is to be accorded the widest scope consistent with the principles and novel features disclosed herein.

What is claimed is:

1. A method, comprising:
analyzing a structure of a first portion of an object;
analyzing a composition of the first portion of the object; and
generating a three-dimensional model of the object, the three dimensional model including data based on the structure of the first portion of the object and data based on the composition of the first portion of the object;
wherein the three-dimensional model comprises a number of voxels, each voxel representing and corresponding to a particular location in three-dimensional space within the object;
wherein each voxel comprises location information specifying a particular location of that voxel in three-dimensional space; and
wherein each voxel corresponding to a location in the first portion of the object also specifies both physical attributes and chemical attributes, including composition, of that location within the object.

2. The method of claim 1, where the data based on the structure of the first portion of the object describes both internal and surface structure of the first portion of the object.

3. The method of claim 1, where the data based on the composition of the first portion of the object describes both internal and surface composition of the object.

4. The method of claim 1, wherein the data based on the structure of the first portion of the object and the data based on the composition of the first portion of the object are both determined using a single X-ray fluorescence spectroscopy system.

5. The method of claim 1, further comprising:
analyzing a structure of a second portion of the object; and
analyzing a composition of the second portion of the object,
where the three-dimensional model of the object also includes data based on the structure of the second portion of the object and data based on the composition of the second portion of the object;
wherein each voxel corresponding to a location in the second portion of the object also specifies both physical attributes and chemical attributes, including composition, of that location within the object.

6. The method of claim 1, where the first portion of the object is represented in the three dimensional-model as a voxel having a set of physical attributes based on the structure of the first portion of the object, and a set of chemical attributes based on the composition of the first portion of the object.

7. A system, comprising:
an analysis module comprising at least one scanner to analyze a structure of an object and to analyze compositions of components of the object; and
a modeling module comprising a processor receiving input from the analysis module to generate a three-dimensional model of the object based on the structure of the object and based on compositions of components of the object; and
an additive manufacturing device to replicate the object by additive manufacture based on the three-dimensional module of the modeling module;
wherein the three-dimensional model comprises a number of voxels, each voxel representing and corresponding to a particular location in three-dimensional space within the object;
wherein each voxel comprises location information specifying a particular location of that voxel in three-dimensional space;
wherein each voxel also specifies both physical attributes and chemical attributes, including composition, of that location within the object; and
wherein the scanner of the analysis module further comprises a surface profiler to profile a surface of the object, the modeling module to incorporate data from the surface profiler into voxels of the three-dimensional model of the object that correspond to the surface of the object.

8. The system of claim 7, where the analysis module determines a chemical composition of components of the object and the structure of the object using a single X-ray fluorescence spectroscopy system.

9. The system of claim 7, where the analysis module performs at least one of optical imaging and scanning, microscopy, x-ray fluorescence (XRF), infrared spectroscopy, raman spectroscopy, ultra-violet spectroscopy, ultra-violet-visible spectroscopy, and laser induced breakdown spectroscopy on the components of the object.

10. The system of claim 7, wherein the additive manufacturing device is configured to use multiple different materials when replicating the object.

11. The system of claim 7, wherein the scanner of the analysis module comprises an x-ray configured to provide output characterizing both the structure and the composition of the object.

12. The system of claim 7, further comprising a design module having a user interface to receive user input to modify the three-dimensional model of the object.

13. The system of claim 7, wherein the analysis module comprises a first scanner for characterizing a structure of the object and a second, different scanner for characterizing a composition of the object.

14. A 3D modeler, comprising:

a structure analysis module to analyze a physical structure of an object, including material density at various locations in the object;

a composition analysis module to analyze a composition of the object;

a modeling module to generate a three-dimensional model of the object, where the three-dimensional model includes data describing physical attributes of the object, including material density at various locations in the object, that are generated based on the physical structure of the object, and where the three-dimensional model includes data describing the composition of the object;

wherein the three-dimensional model comprises a number of voxels, each voxel representing and corresponding to a particular location in three-dimensional space within the object;

wherein each voxel comprises location information specifying a particular location of that voxel in three-dimensional space; and wherein each voxel also specifies both physical attributes, including material density, and chemical attributes, including composition, of the corresponding location within the object.

15. The 3D modeler of claim 14, comprising a design module, to facilitate modifying the three-dimensional model of the object by changing one or more of a physical structure of a component of the three-dimensional model, and a composition of a component of the three-dimensional model.

16. The 3D modeler of claim 14, comprising a surface profiler to analyze surface roughness of the object and where the modeling module generate the three-dimensional model of the object so that a surface components of the three-dimensional model have a surface roughness that corresponds to the surface roughness of the object.

17. The 3D modeler of claim 14, wherein the data describing physical attributes, including material density, and the data describing the composition of the object are both determined using a single X-ray fluorescence spectroscopy system.

18. The 3D modeler of claim 14, where the physical attributes of the voxels include size attributes.

* * * * *